(12) United States Patent
Fritz-Langhals et al.

(10) Patent No.: US 9,181,284 B2
(45) Date of Patent: Nov. 10, 2015

(54) METHOD FOR PRODUCING AMINOALKYLALKOXYSILANES

(71) Applicant: Wacker Chemie AG, Munich (DE)

(72) Inventors: Elke Fritz-Langhals, Ottobrunn (DE); Sotirios Kneissl, Munich (DE); Juergen Stohrer, Pullach (DE)

(73) Assignee: Wacker Chemie AG, Munich (DE)

(*) Notice: Subject to any disclaimer, the term of this patent is extended or adjusted under 35 U.S.C. 154(b) by 0 days.

(21) Appl. No.: 14/386,167

(22) PCT Filed: Mar. 6, 2013

(86) PCT No.: PCT/EP2013/054503
§ 371 (c)(1),
(2) Date: Sep. 18, 2014

(87) PCT Pub. No.: WO2013/139604
PCT Pub. Date: Sep. 26, 2013

(65) Prior Publication Data
US 2015/0051418 A1    Feb. 19, 2015

(30) Foreign Application Priority Data

Mar. 19, 2012    (DE) .......................... 10 2012 204 315

(51) Int. Cl.
*C07F 7/10* (2006.01)
*C07F 7/18* (2006.01)

(52) U.S. Cl.
CPC ............... *C07F 7/188* (2013.01); *C07F 7/1844* (2013.01)

(58) Field of Classification Search
USPC ......................................... 556/410, 452, 471
See application file for complete search history.

(56) References Cited

U.S. PATENT DOCUMENTS

| 4,045,460 | A | 8/1977 | Kleinstuck |
| 7,659,418 | B2 | 2/2010 | Ramdani et al. |
| 2005/0245755 | A1 | 11/2005 | Ramdani et al. |
| 2011/0009558 | A1 | 1/2011 | Maliverney et al. |
| 2012/0190876 | A1* | 7/2012 | Gohndrone et al. .......... 556/424 |

FOREIGN PATENT DOCUMENTS

| DE | 60315982 T2 | 5/2008 |
| JP | 2003246789 A | 9/2003 |
| PL | 145671 B1 | 10/1988 |
| PL | 162752 B1 | 1/1994 |

OTHER PUBLICATIONS

Gulinski et al., Synthesis of Organofunctional Silanes with Sterically Hindered Substituents at Silicon Atoms; Applied Organometallic Chemistry, 2001: 15: pp. 649-657.
Speier et al., Synthesis of (3-Aminoalkyl)silicon Compounds; Journal of Organic Chemistry, vol. 36, No. 21, 1971, pp. 3120-3126.

* cited by examiner

*Primary Examiner* — Sudhakar Katakam
*Assistant Examiner* — Pancham Bakshi
(74) *Attorney, Agent, or Firm* — Brooks Kushman P.C.

(57) ABSTRACT

Aminoalkylalkoxysilanes are prepared from halo(haloalkyl)silanes in the simultaneous presence of ammonia or primary organic amine and alcohol.

5 Claims, No Drawings

METHOD FOR PRODUCING AMINOALKYLALKOXYSILANES

CROSS-REFERENCE TO RELATED APPLICATIONS

This application is the U.S. National Phase of PCT Appln. No. PCT/EP2013/054503 filed Mar. 6, 2013, which claims priority to German application DE 10 2012 204 315.2 filed Mar. 19, 2012, the disclosures of which are incorporated in their entirety by reference herein.

BACKGROUND OF THE INVENTION

1. Field of the Invention

The invention relates to the production of aminoalkylalkoxy-silanes from the corresponding halo(haloalkyl)silanes by reaction with ammonia or organic amines and with alcohol.

2. Description of the Related Art

Aminoalkylalkoxysilanes are important intermediates in the industry. The amine functionality permits linking with further synthesis building blocks, for example for the formation of copolymers. Alkoxy groups on the silicon assume the function of binding to polysiloxane backbones.

Starting materials for the synthesis of the aminoalkylalkoxysilanes are usually the corresponding alkoxy(haloalkyl)silanes, which are converted to the aminoalkylalkoxysilanes using ammonia or organic amines. The alkoxy(haloalkyl)silanes required as chemical precursors for the amination are produced in the procedure via a separate, independent alkoxylation procedure.

Both alkoxylation and amination are each technically complex methods which can only be carried out in special apparatus. The alkoxylations require apparatus resistant to halohydric acids. Secondary reactions, for example, formation of water during reaction of alcohol with formed hydrogen halide to give alkyl halide can only be prevented by special methods, e.g. countercurrent methods, which ensure that hydrogen halide is removed quickly from the reaction mixture. DE 60315982 T2 equivalent to U.S. Pat. No. 7,659,418, describes, for example, an apparatus for producing 3-chloropropylalkoxysilanes from the corresponding chloro(3-chloropropyl)silanes according to the countercurrent principle. JP 2003246789 describes the use of ammonia or organic amines in the alkoxylation, but this serves only for the removal of hydrogen chloride during the synthesis of the corresponding alkoxychloroalkylsilanes.

Animations, by contrast, require apparatus apparatus which is stable in basic environments. Due to low boiling point of especially ammonia and low molecular weight amines, these reactions are carried out industrially in steel autoclaves, in most cases under high pressure, to achieve short reaction times and/or high conversion. Fundamental work on this is described by Speier et al. in J. Org. Chem. 1971, 36, 3120-3126. Furthermore, aminoalkylalkoxysilanes—as likewise reported in J. Org. Chem. 1971, 36, 3120-3126—can be obtained by alcoholysis of silazanes.

DE 2521399, equivalent to U.S. Pat. No. 4,045,460, describes the synthesis of aminoalkylalkoxysilanes proceeding from tri- and dialkoxy(chloroalkyl)silanes in the presence of alcohol as solvent addition. The added alcohol does not participate in the reaction but serves only as an inert additive. The starting material is the corresponding alkoxysilanes which have been produced via an independent reaction step.

SUMMARY OF THE INVENTION

It has now been unexpectedly and surprisingly discovered that halo(haloalkykl)silanes can be converted to aminoalkylalkoxysilanes in the simultaneous presence of ammonia or primary organic amine and alcohol, which results in higher yields of monoalkylated products, and thus provides for a more economical and efficient process.

DETAILED DESCRIPTION OF THE PREFERRED EMBODIMENTS

The invention provides a method for synthesizing aminoalkylalkoxysilanes of the general formula I $$RR'N-X-Si(R^1)_n(OR^2)_{3-n} \qquad I,$$

and hydrohalides thereof,
by reacting the halo(alkylhalo)silanes of the general formula II $$Y-X-Si(R^1)_nZ_{3-n} \qquad II,$$

with ammonia or an organic amine of the general formula III, $$R-NH-R' \qquad III,$$

and an alcohol of the general formula IV, $$R^2-OH,$$

where
R and R' represent hydrogen or hydrocarbon radicals having 1 to 12 carbon atoms, where nonadjacent carbon atoms can be replaced by nitrogen or oxygen atoms,
$R^1$ represents a hydrocarbon radical having 1 to 8 carbon atoms, where nonadjacent carbon atoms can be replaced by oxygen,
$R^2$ represents an alkyl group having 1 to 8 carbon atoms, where nonadjacent carbon atoms can be replaced by oxygen,
X is a divalent alkyl group having 1 to 12 carbon atoms,
Y and Z are halogen, and
n is 0, 1, or 2.

The conversion of the halo(haloalkyl)silanes to the aminoalkylalkoxysilanes of the general formula I is carried out in the presence of ammonia or organic amine and alcohol. This procedure considerably simplifies the synthesis of the aminoalkylalkoxysilanes of the general formula I and thus leads to an increase in economic feasibility.

It has been surprisingly been found that the presence of an alcohol in a reaction mixture basic due to the presence of ammonia or amine does not lead, to a noteworthy exchange of the organically bound chlorine by alkoxy groups with the formation of alkoxyalkylsilanes as was initially expected. Although these products can be detected in the reaction mixtures, their fraction is very low and is generally less than 1%.

Moreover, it has been surprisingly been found that as a result of the simultaneous presence of alcohol and ammonia or primary organic amine during the amination, higher yields of aminoalkylalkoxysilanes of the general formula I are obtained than if a reaction of the halo(haloalkyl)silanes with ammonia or organic amines is carried out first and the reaction products are then converted with alcohol into the aminoalkylalkoxysilanes of the general formula I. As a result of the simultaneous presence of alcohol and ammonia or organic amine, lower fractions of the double nitrogen-alkylated products $HN[X-Si(R^1)_n(OR^2)_{3-n}]_2$, or $RN[X-Si(R^1)_n(OR^2)_{3-n}]_2$ are formed.

When using ammonia, as a result of the simultaneous presence of alcohol, moreover, the fraction of triple nitrogen-alkylated products $N[X-Si(R^1)_n(OR^2)_{3-n}]_3$ is reduced. This leads to higher yields of the desired aminoalkylalkoxysilane of the general formula I. High yields of monoalkylated products are usually achieved by using a large excess of ammonia or organic amine. In the presence of alcohol, on account of the increased selectivity of the reaction, smaller excess of ammonia or organic amine is sufficient, which leads to enhanced space-time output of the process.

Finally, the addition of alcohol—particularly when using low-boiling aminic reactants such as ammonia or methylamine—at a given reaction temperature causes a significant reduction in the resulting reaction pressure when compared to the instruction given in J. Org. Chem. 1971, 36, 3120-3126. Consequently, the method according to the invention can be also carried out in pressurized reactors which have a lower pressure stability and a significantly less complex construction.

Moreover, the method offers the advantage that the ammonium halide, which formed, remains partially or even completely dissolved in the presence of alcohol so that the caking of ammonium chloride or amine hydrochlorides that hinder the reaction, and are described for example in EP 1295889 for aminations, are avoided.

Preferably, R and R', independently represent hydrogen or an unbranched, branched, or cyclic saturated or unsaturated alkyl group, aryl group, or aralkyl group. Preferably, R and R' have 1 to 6 carbon atoms. More preferably, R and R' represent hydrogen or an alkyl group having 1 to 6 carbon atoms, where nonadjacent carbon atoms can be replaced by nitrogen.

Examples of compounds of the general formula III are ammonia, methylamine, ethylamine, n-propylamine, isopropylamine, n-butylamine, isobutylamine, tert-butylamine, cyclohexylamine, 1,2-diaminoethane, 1,2-diaminopropane, 1,3-diaminopropane, or 1,4-diaminobutane.

Preferably, X is a divalent unbranched, branched, or cyclic saturated or unsaturated alkyl group having 1 to 12 carbon atoms. More preferably, X is a divalent unbranched or branched alkyl group having 1 to 8 more preferably 1 to 4, most preferably 2 or 3 carbon atoms.

$R^1$ preferably represents a linear, branched, or cyclic, saturated or unsaturated alkyl group having 1 to 8 carbon atoms aryl radical, or aralkyl radical. Preferably, $R^1$ represents a saturated or unsaturated alkyl group having 1 to 6 carbon atoms or an aryl radical. More preferably, $R^1$ represents an alkyl group having 1 to 4 carbon atoms, a vinyl group or a phenyl group, most preferably, $R^1$ represents a methyl group.

Preferably, $R^2$ represents a linear or branched alkyl group having 1 to 8 carbon atoms, where nonadjacent carbon atoms can be replaced by oxygen. More preferably, $R^2$ represents a linear or branched alkyl group having 1 to 5 carbon atoms, where preferably 1 to 2 carbon atoms can be replaced by oxygen. Particular preference is given to alkyl groups with 1 to 5 carbon atoms, where preferably 1 carbon atom is replaced by oxygen.

Examples of radicals $R^2$ are methyl, ethyl, n-propyl, isopropyl 2-methoxyethyl, or 2-methoxypropyl.

Preferably, Y is Cl or Br, more preferably Cl.
Preferably, Z is Cl or Br, more preferably Cl.

The method is preferably carried out at temperatures of at least 30° C., more preferably at least 50° C., and most preferably at least 70° C., and preferably at most 230° C., more preferably at most 200° C., most preferably at most 170° C.

The reaction time for the production of the aminoalkylalkoxysilanes of the general formula I is preferably at least 5 minutes, more preferably at least 10 minutes, most preferably at least 20 minutes, and preferably at most 100 hours, more preferably at most 30 hours, and most preferably at most 15 hours.

The pressure during the production of the aminoalkylalkoxysilanes of the general formula I is preferably at least 1 bar and at most 200 bar, more preferably at most 120 bar, most preferably at most 90 bar. All of the stated pressure valves are absolute values.

The method can be carried out, for example, as a batch reaction, as a semibatch reaction, or continuously.

For example, the reactants can be mixed simultaneously. Preferably, the alcohol of the general formula IV and ammonia or organic amine of the general formula III can be introduced in the form of a mixture and then admixed with the silane of the general formula II. This can take place at ambient temperature or at elevated temperature. More preferably, the addition of the silane of the general formula II takes place at elevated temperature.

Preferably, the reaction is carried out by mixing. Here, the mixing methods known to the person skilled in the art can be used. For example, the mixing can take place by stirring. The reaction can be carried out continuously. The technical configurations known to the person skilled in the art are suitable, for example, tubular reactors, loop reactors, or stirred-tank cascades.

Preferably, ammonia or organic amine of the general formula III is used at least in the stoichiometric amount of the molar halogen fraction Y and Z of the silane of the general formula II. However, more preferably, an excess of at least 2 equivalents based on the molar amount of halogenfraction Y and Z of the silane of the general formula II is used since as a result—as explained above—higher yields of the desired monoalkylation products of the general formula I are formed. When using ammonia, an excess of at least 5 equivalents is preferred. The excess of used ammonia or organic amine of the general formula III is preferably at most 200 equivalents, particularly preferably at most 100 equivalents.

Preferably, the alcohol of the general formula IV is used at least in a stochiometric amount of the molar fraction of the group Z in the silane of the general formula II. More preferably, amounts of alcohol of at least 1.1 equivalents, most preferably of at least 1.5 equivalents are used. Preferably, the alcohol of the general formula IV is used in a molar amount of the group Z in the silane of the general formula II of at most 30 equivalents, more preferably of at most 15 equivalents.

Further components, for example, solvents, can be used in weight fractions of at least 1% and at most 500%, preferably at least 10% and at most 100%, based on the total reaction mass. These components can be added before, during, or after the reaction. They are preferably inert, i.e. no reaction with the reactants takes place. Examples of preferred solvents are saturated or olefinically or aromatically unsaturated linear or branched hydrocarbons having acyclic or cyclic groups, ethers, nitriles, sulfoxides, sulfones, or aryl- and alkyl-terminated siloxanes. Examples of preferred solvents are the $C_5$ to $C_{30}$ n-alkanes or their isomers or isomer mixtures, Shellsol® or Sarasol® from Shell, solvents of the Hydroseal®, Isane®, Ketrul®, Kerdane®, Spirdane®, or Solvarex® series from Total, heat transfer oils, e.g. Marlotherm® SH from AVIA, $\alpha,\omega$-bis(trimethylsilyl)-terminated poly(dimethylsiloxanes), for example the WACKER AK oils, methyl tert-butyl ether, tetrahydrofuran,1,4-dioxane, ethylene glycol dibutyl ether, dioctyl ether, diphenyl ether, dibenzyl ether, isomeric ditolyl ethers, preferably as isomer mixtures. Preference is given to solvents whose boiling point differs from the boiling point of the aminoalkylalkoxysilane so much that simple distillative separation is possible. Preferably, the boiling point of these solvents at atmospheric pressure is at least 10 K higher.

At the end of the reaction, the aminoalkylalkoxysilane of the general formula I is present partially or completely as ammonium alkylalkoxysilane halide. Isolation of the aminoalkylalkoxysilane of the general formula I can take place by a method known to the person skilled in the art. The separation from ammonium halide formed during the reaction can take place, for example, by crystallization. Precipitants, for example, organic solvents, can be also added. Another option is adding suitable bases which convert the ammonium alkyl-alkoxysilane halide into the aminoalkylalkoxysilane after the reaction. The suitable methods known to the person skilled in the art for product isolation can, if appropriate, be also combined.

In a preferred embodiment, after the reaction, alkali metal alcoholate, for example, sodium methylate, is added as a base to the reaction mixture, the formed solid alkali metal halide is separated, for example, by filtration or by centrifugation, and the liquid phase is fractionally distilled for the isolation in a pure state of the product of the general formula I.

All of the above symbols in the formulae above have their meanings in each case independent of one another. In all of the formulae, the silicon atom is tetravalent.

In the examples which follow, unless stated otherwise in each case, all quantitative data and percentages are based on the weight; all pressures are 0.10 MPa (abs.) and all temperatures are 20° C.

EXAMPLE 1

A 1 L autoclave is charged with 212 g (6.63 mol) of methanol, 269 g (15.8 mol) of ammonia liquid are introduced, and the mixture is heated to 133° C. In doing so, a pressure of 54 bar is reached. 92.4 g (0.54 mol) of chloro(3-chloropropyl)-dimethylsilane are added in 20 min, and the mixture is left to react at 133° C. for additional 70 min. After cooling, the reaction mixture is analyzed by NMR spectroscopy in d4-methanol: relative fraction of (3-aminopropyl)methoxydimethyl-silane 88%, di-3-(dimethylmethoxysilyl)propylamine 12%, tri-3-(dimethylmethoxysilyl)propylamine about 0.5%; conversion 99.7%. The reaction mixture is neutralized with 194 g of a 30% strength sodium methylate solution in methanol, filtered off from the solid, and the solution is subjected to fractional distillation.

Yield 63 g (79%), purity>99.5%.

EXAMPLE 2

As in example 1, 100 g (584 mmol) of chloro(3-chloropropyl)-dimethylsilane are reacted with 298 g (17.5 mol) of ammonia and 122 g (3.81 mol) of methanol, the dosage time is 84 min. After adding 253 g (1.17 mol) of sodium methylate solution, the reaction mixture is analyzed by gas chromatography: (3-aminopropyl)methoxydimethylsilane 88%, di-3-(dimethyl-methoxysilyl)propylamine 12%, (3-methoxypropyl)methoxydimethyl-silane 0.3%.

EXAMPLE 3

A 1 L autoclave is charged with 196 g (6.13 mol) of methanol, 255 g (15.0 mol) of ammonia liquid are introduced and the mixture is heated to 133° C. In doing so, a pressure of 53 bar is reached. 171 g (1.00 mol) of chloro-(3-chloropropyl)-dimethylsilane are added in 2 hours, and the mixture is left to react at 133° C. for additional 30 min. After cooling, the reaction mixture is analyzed by NMR spectroscopy in d4-methanol: relative fraction of (3-aminopropyl)methoxydimethylsilane 76%, di-3-(dimethylmethoxysilyl)propylamine 23%, tri-3-(dimethylmethoxysilyl)propylamine about 2%; conversion >99.7%. The reaction mixture is rendered alkaline with 30% strength sodium methylate solution in methanol, and the clear product solution is analyzed by gas chromatography: (3-aminopropyl)methoxydimethylsilane 76%, di-3-(dimethyl-methoxysilyl)propylamine 23%, tri-3-(dimethylmethoxysilyl)-propylamine 2%; (3-methoxypropyl)methoxydimethylsilane 0.2%.

COMPARATIVE EXAMPLE 3

Not According to the Invention

A 1 L autoclave is charged with 273 g (16.1 mol) of ammonia liquid and the mixture is heated to 131° C. In doing so, a pressure of 99 bar is reached. 171 g (1.00 mol) of chloro(3-chloropropyl)dimethylsilane are added in 70 min, and the mixture is left to react at 130° C. for additional 85 min. At 37 to 45° C., 720 g of 15% strength sodium methylate solution in methanol are pumped into the reaction mixture. After cooling, the clear reaction solution is analyzed by gas chromatography: relative fraction of (3-aminopropyl)methoxydimethylsilane 55%, di-3-(dimethylmethoxysilyl)propylamine 39%, tri-3-(dimethylmethoxysilyl)propylamine 6%.

EXAMPLE 4

A 1 L autoclave is charged with 196 g (6.13 mol) of methanol, 259 g (15.2 mol) of ammonia liquid are introduced and the mixture is heated to 144° C. In doing so, a pressure of 69 bar is reached. 171 g (1.00 mol) of 3-chloropropyldimethylchlorosilane are added in 1 hour, and the mixture is left to react at 144-148° C. for additional 30 min. The pressure at the end of the reaction is 62 bar. At 40-50° C., ammonia is discharged, and the reaction mixture is diluted with 170 g of methanol. After cooling, the reaction mixture is analyzed by NMR spectroscopy in d4-methanol: relative fraction of (3-aminopropyl)methoxydimethylsilane 77%, di-3-(dimethyl-methoxysilyl)propylamine 21%, tri-3-(dimethylmethoxysilyl)-propylamine 2%; conversion>98.5%. The reaction mixture is rendered alkaline with 30% strength sodium methylate solution and the clear product solution is analyzed by gas chromatography: (3-aminopropyl)methoxydimethylsilane 76%, di-3-(dimethylmethoxysilyl)propylamine 23%, tri-3-(dimethylmethoxy-silyl)propylamine 1%, (3-methoxypropyl)methoxydimethylsilane 0.3%.

EXAMPLE 5

A 1 L autoclave is charged with 137 g (4.28 mol) of methanol, 265 g (15.6 mol) of ammonia liquid are introduced and the mixture is heated to 133° C. In doing so, a pressure of 68 bar is reached. 171 g (1.00 mol) of chloro(3-chloropropyl)dimethylsilane are added in 2 hours and the mixture is left to react at 133-135° C. for an additional 60 min. The pressure at the end of the reaction is 54 bar. Ammonia is evaporated at about 40-50° C., and then 630 g (3.5 mol) of a 30% strength sodium methylate solution in methanol are pumped into the autoclave. The reaction solution is analyzed by NMR spectroscopy in d4-methanol: relative fraction of (3-aminopropyl)methoxydimethylsilane 73%, di-3-(dimethyl-methoxysilyl)propylamine 26%, tri-3-(dimethylmethoxysilyl)-propylamine 1%, conversion 97%.

EXAMPLE 6

At 74° C., 7.0 kg (40.9 mol) of chloro(3-chloropropyl)dimethylsilane are added to 25.0 kg (781 mol) of methanol and 21.0 kg (1240 mol) of ammonia, and the reaction mixture is heated at 75 to 80° C. for 23 hours. The pressure is about 13 bar. A sample of the reaction solution is analyzed by NMR spectroscopy in d4-methanol: relative fraction of (3-aminopropyl)methoxydimethylsilane 80%, di-3-(dimethylmethoxysilyl)propylamine 20%, conversion>99.9%.

The mixture is left to cool, and ammonia is discharged into a scrubber, the reaction solution is admixed with 17.7 kg (81.9 mol) of a 25% strength solution of sodium methylate in methanol and the solid formed (sodium chloride) is filtered off. Fractional distillation gives 4.1 kg (69%) of (3-aminopropyl)dimethylmethoxysilane in a purity of 99.2%.

EXAMPLE 7

As in example 5, 92.4 g (0.540 mol) of chloro(3-chloropropyl)dimethylsilane are reacted with 269 g (15.8 mol) of ammonia and 212 g (6.62 mol) of methanol. The dosage time is 20 min, the after-reaction time 70 min. The reaction solution is analyzed by NMR spectroscopy in d4-methanol: relative fraction of (3-aminopropyl)methoxydimethylsilane 82%, di-3-(dimethyl-ethoxysilyl)propylamine 18%, conversion>99%.

EXAMPLE 8

As in example 5, 171 g (1.0 mol) of chloro(3-chloropropyl)di-methylsilane are reacted with 260 g (15.3 mol) of ammonia and 137 g (4.28 mol) of methanol. The dosage time is 117 min, the after-reaction time 60 min. Following reaction with sodium methylate solution (561 g, 2.00 mol) as in ex. 5, the reaction solution is analyzed by NMR spectroscopy in d4-methanol: relative fraction of (3-aminopropyl)methoxydimethylsilane 74%, di-3-(dimethylmethoxysilyl)propylamine 26%, tri-3-(dimethyl-ethoxysilyl)propylamine 1%; conversion about 99%.

EXAMPLE 9

Ethanol

A 1 L autoclave is charged with 169 g (3.67 mol) of technical-grade absolute ethanol, 233 g (13.7 mol) of ammonia liquid are introduced, and the mixture is heated to 134° C. 146 g (0.85 mol) of chloro(3-chloropropyl)dimethylsilane are added in 110 min, and the mixture is left to react at 133° C. for an additional 90 min. The end pressure is 60 bar. Ammonia is evaporated at 42-48° C., and then 581 g (1.71 mol) of a 20% strength sodium methylate solution in ethanol are pumped into the autoclave and left to react at 56 to 72° C. for 45 min. The reaction solution is analyzed by NMR spectroscopy in d4-methanol: relative fraction of (3-aminopropyl)ethoxydimethylsilane 69%, di-3-(dimethylmethoxysilyl)propylamine 29%, tri-3-(dimethyl-methoxysilyl)propylamine 2%; conversion quantitative.

EXAMPLE 10

N-butylamine 10.0 g (58.4 mmol) of chloro(3-chloropropyl)dimethylsilane are added, under argon while stirring, to a mixture of 10.7 g (146 mmol) of n-butylamine and 8.0 g (250 mmol) of methanol.

The mixture is heated to 83° C. and stirred overnight at this temperature. 25.9 g (0.12 mol) of a 25% strength sodium methylate solution in methanol are added and the reaction solution is analyzed by gas chromatography: relative fraction of 3-(N-butylamino)propylmethoxydimethylsilane 85%, di-3-(dimethylmethoxysilyl)-N-butylpropylamine 15%, conversion 98%.

EXAMPLE 11

Ethylenediamine

At 60° C., 10.0 g (58.4 mmol) of chloro(3-chloropropyl)di-methylsilane are added, under argon while stirring, into a mixture of 13.9 g (323 mmol) of dry ethylenediamine and 12.0 g (375 mmol) methanol in 16 min, during which the temperature increases temporarily to 80° C. Following the addition, the mixture is heated to 86° C. and stirred at this temperature for 18 hours. 25.5 g (118 mmol) of a 25% strength sodium methylate solution in methanol are then added, and the reaction solution is analyzed by gas chromatography: 97% (N-aminoethyl)aminopropyl-methoxydimethylsilane, 2% MeO—SiMe$_2$CH$_2$CH$_2$CH$_2$—NH—CH$_2$—CH$_2$—NH—CH$_2$CH$_2$CH$_2$—Me$_2$Si—OMe.

EXAMPLE 12

Methylamine

A mixture of 277 g (6.02 mol) of absolute ethanol and 137 g (4.41 mol) of methylamine is heated to 103° C. in the autoclave. While stirring, 75.3 g (0.442 mol) of chloro(3-chloropropyl)dimethylsilane are added in 65 min, during which the temperature increases to 106° C. The pressure is 7 bar. Following the addition, the mixture is heated at 98-106° C. for an additional 2 hours and then cooled to 40° C. 301 g (0.885 mol) of a 20% strength sodium ethylate solution are then added, and the mixture is stirred at 56 to 83° C. for a additional 45 min. Gas chromatographic analysis of the reaction solution reveals 86% N-methylaminopropylmethoxydimethylsilane and 5% MeO—SiMe$_2$CH$_2$CH$_2$CH$_2$—N(CH$_3$)—CH$_2$CH$_2$CH$_2$—Me$_2$Si—OMe.

The invention claimed is:
1. A method for synthesizing an aminoalkylalkoxysilane of the formula I

$$RR'N—X—Si(R^1)_n(OR^2)_{3-n} \qquad I,$$

and hydrohalides thereof, comprising:
reacting at least one halo(alkylhalo)silane of the formula II $$Y—X—Si(R^1)_nZ_{3-n} \qquad II,$$

with ammonia or at least one organic amine of the formula III, $$R—NH—R' \qquad III,$$

and at least one alcohol of the formula IV, $$R^2—OH,$$

where
R and R' represent hydrogen or a hydrocarbon radical having 1 to 12 carbon atoms, where nonadjacent carbon atoms are optionally replaced by nitrogen or oxygen atoms,
$R^1$ represents a hydrocarbon radical having 1 to 8 carbon atoms, where nonadjacent carbon atoms are optionally replaced by oxygen,
$R^2$ represents an alkyl group having 1 to 8 carbon atoms, where nonadjacent carbon atoms are optionally replaced by oxygen,
X is a divalent alkyl group having 1 to 12 carbon atoms,
Y and Z are halogen, and
n is 0, 1, or 2.

2. The method of claim 1, wherein R and R' represent hydrogen or an alkyl group having 1 to 6 carbon atoms, where nonadjacent carbon atoms are optionally replaced by oxygen.

3. The method of claim 1, wherein $R^2$ is selected from the group consisting of methyl, ethyl, n-propyl, isopropyl, 2-methoxyethyl and 2-methoxypropyl, and mixtures thereof.

4. The method of claim 1, wherein Y and Z are selected from the group consisting of Cl, Br, and mixtures thereof.

5. The method of claim 1, wherein ammonia or organic amine of the formula III is used in an excess of at least 2 equivalents based on moles of halogen Y and Z of the silane of the formula II.

* * * * *